(12) United States Patent
Bernard et al.

(10) Patent No.: US 6,537,499 B1
(45) Date of Patent: Mar. 25, 2003

(54) METHOD AND DEVICE FOR IDENTIFICATION OF A SUBSTANCE

(75) Inventors: Andre Bernard, Zurich (CH); Hans Biebuyck, Rockville, MD (US); Emmanuel Delamarche, Adliswil (CH); Bruno Michel, Adliswil (CH); Heinz Schmid, Waedenswil (CH)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 09/315,804

(22) Filed: May 21, 1999

(30) Foreign Application Priority Data

Feb. 6, 1998 (EP) .............................................. 98109964

(51) Int. Cl.[7] .............................................. G01N 21/47
(52) U.S. Cl. ........................ 422/82.05; 422/50; 422/63; 422/68.1; 436/501; 436/513; 436/518; 436/43
(58) Field of Search ................... 422/82.05, 82.11, 422/68.1, 63; 435/6, 501; 250/306, 307; 73/105; 436/501, 513, 518, 43

(56) References Cited

U.S. PATENT DOCUMENTS

| 3,960,489 A |   | 6/1976  | Giaever |         |
|-------------|---|---------|---------|---------|
| 3,993,742 A |   | 11/1976 | Rey et al. |      |
| 4,002,056 A |   | 1/1977  | Kopito et al. |   |
| 5,354,985 A | * | 10/1994 | Quate ......................... 250/234 |
| 5,363,697 A | * | 11/1994 | Nakagawa .................... 73/105 |
| 5,372,930 A | * | 12/1994 | Colton et al. ................... 435/6 |
| 5,394,741 A | * | 3/1995  | Kajimura et al. .............. 73/105 |
| 5,620,857 A |   | 4/1997  | Weetall et al. |  |
| 5,730,940 A | * | 3/1998  | Nakagawa ................. 422/68.1 |
| 5,807,758 A | * | 9/1998  | Lee et al. .................... 436/526 |
| 5,939,709 A | * | 8/1999  | Ghislain et al. ............. 250/216 |
| 5,969,821 A | * | 10/1999 | Muramatsu et al. ........ 356/376 |
| 5,982,009 A | * | 11/1999 | Hong et al. .................. 257/414 |
| 6,006,593 A | * | 12/1999 | Yamanaka .................... 73/105 |
| 6,057,547 A | * | 5/2000  | Park et al. ................... 250/307 |
| 6,104,030 A | * | 8/2000  | Chiba et al. ................. 250/306 |
| 6,118,121 A | * | 9/2000  | Ando et al. .................. 250/206 |
| 6,123,819 A | * | 9/2000  | Peeters ........................ 204/403 |
| 6,146,593 A | * | 11/2000 | Pinkel et al. ............... 422/68.1 |
| 6,165,335 A | * | 12/2000 | Lennox et al. .............. 204/403 |
| 6,325,904 B1 | * | 12/2001 | Peeters ........................ 204/403 |

OTHER PUBLICATIONS

Florin, E., et al, Adhesion Forces Between Individual Ligand–Receptor Pairs, Science, vol. 264, Apr. 15, 1994.

Binnig, G., et al, Atomic Force Microscope, Physical Review Letters, vol. 56, No. 9, Mar. 3, 1986.

Chaudhury, M., et al, Direct Measurement of Interfacial Interactions between Semispherical Lenses nd Flat Sheets, Langmuir, vol. 7, No. 5, 1991.

* cited by examiner

Primary Examiner—Jill Warden
Assistant Examiner—Brian Sines
(74) Attorney, Agent, or Firm—Whitham, Curtis & Christofferson, P.C.; Stephen C. Kaufman

(57) ABSTRACT

A method and also a device is proposed for identification of a substance, preferably comprising biochemical molecules. In a first step a probe and said substance will be brought into contact, afterwards in a second step the probe and said substance will be withdrawn from each other, while measuring the value of at least one physical parameter characterizing the interaction between said probe and said substance and comparing said measured value with a reference value for identification.

17 Claims, 3 Drawing Sheets

METHOD AND DEVICE FOR IDENTIFICATION OF A SUBSTANCE

TECHNICAL FIELD

The present invention relates to a method as well as a device for identification of a substance, preferably comprising biochemical molecules. In particular, it is the aim of the present invention to improve the technique of analyzing unknown biomolecules for achieving results in an easier and quicker way so that the method can be used without investing great effort and high costs. A preferred embodiment of the invention is a biosensor for easy detection of unknown biomolecules.

BACKGROUND OF THE INVENTION

Many approaches have been undertaken for determining the type of substance such as a chemical substance, in particular a biomolecule, which provides a very high degree of selective binding properties.

There are methods of analyzing the optical properties of individual substances such as absorption or transmission behavior, all these methods require very accurate measurement equipment comprising light sources for emitting defined wavelengths as well as very accurate detection devices, rendering these methods very expensive:

Methods are known for identification of substances by measuring their surface properties such as surface forces or work of adhesion. The work of adhesion of a substance coated onto a solid surface can be determined by measuring the contact angle between the surface and a fluid droplet applied onto it. This technique is described in an article by Israelachvili, "Interfacial Forces", J.Vac.Sci. Technol. A 10(5), September/October 1992, pp. 2961–2971.

Another approach for estimating the surface free energies of solid surfaces requires direct examination of solid-solid interfaces. In an article by Chaudhury and Whitesides, Langmuir, vol. 7,. No. 5, 1991, pp. 1013–1025, measurement of the surface free energy of elastomeric polymers is deduced by measurement of the deformation of semispherical lenses of poly-dimethylsiloxane elastomers and their chemical derivatives. Analyses of the deformation of the lens were conducted using Young's equation and the Johnson, Kendall Roberts (YRK) model. The analyses included balancing the adhesion forces acting across the interface with the restoring forces that oppose the deformation of the lens. Accurate results require the Young's modulii and the Poisson ratios of each material. In addition, spherical lenses with a well-defined radius and smooth surface have to be produced for one or both materials involved in the measurement.

By determining the work of adhesion of unknown substances which are derivatized onto a sample surface, an estimation can be made about the nature and the type of the derivatized substance. However, the aforementioned methods are complicated and drawn out.

Another aspect in determining binding constants of substances by measuring their surface properties is the direct interaction between at least two molecules. Such interactions, derived from multiple weak bonds between geometrically complementary surfaces which are coated with different chemical groups, can be very strong. In the field of biomolecules, the sensitivity of binding properties is very distinct so that molecular recognition between a receptor and a ligand, an antibody and an antigen as well as complementary strands of DNA provides a basis for identification of biochemical substances such as biomolecules.

With the development of scanning probe microscopes, in particular the atomic force microscope (AFM), surfaces can be probed in physiological environments with molecular resolution and forces down to the piconewton range as is disclosed in an article by G. Binnig, C. F. Quate and Ch. Gerber, Phys. Ref. Lett. 56, 930 (1986).

Using the atomic force microscope, Florin et al. measured the adhesion force between the tip of an atomic force microscope cantilever derivatized with avidin and agarose beads functionalized with biotin. They found the force required to separate the tip and the bead to be quantized in integer multiples of 160 pN (E.-L. Florin, V. T. Moy and H. E. Gaub, Science 264, 415 (1994)).

It is an object of the present invention to provide a method for identification of unknown substances which requires less effort with respect to necessary equipment and fewer procedure steps. The method should be easy to control and should produce reliable results.

It is a further object of the present invention to provide a device for identification of substances based on it's binding characteristics to a known probe, in particular comprising a biochemical molecule, without the need of highly sophisticated analyzing devices, which usually are very expensive. Furthermore such a device should be easy to handle and should be used as a biosensor enabling the identification of a plurality of unknown substances.

SUMMARY OF THE INVENTION

The present invention relates to a method for identification of a substance, preferably comprising biochemical molecules, which is usually derivatized onto a sample surface. Furthermore, a well-known probe is used which is favorably derivatized onto a contact surface for the purpose of better handling. Both surfaces coated with the aforementioned layers are brought into contact and then separated from each other while measuring physical parameters characterizing the interaction between said substance and said probe. The obtained results are compared with reference values for identification. These reference values can be listed or measured with reference techniques, for example, as is described above in connection with the cited state of the art.

For characterization and identification of an unknown substance, the binding related work of adhesion is a suitable parameter which can be measured with the aforementioned invented method. In a preferred implementation of the invented method a molded elastomeric pillar is used with a well-defined contact surface onto which a known probe is derivatized. This probe is pushed towards the sample surface onto which the unknown substance, preferably biochemical molecules, is derivatized, until both surfaces have a well-defined conformal contact.

The term "conformal contact" implies that the surface shapes of the two media put on top of each other are similar to such an extent that fluids can essentially not penetrate into the plane where the surfaces meet each other except for immobilized water strongly associated with the molecules. The term "fluid" refers to both liquids and gases.

While both surfaces are brought together until conformal contact is reached the force during this loading phase is determined as a function of the travelling distance from the point of which the two surfaces make the first contact until the state of conformal contact which is indicated by a given force. Subsequently the two surfaces are withdrawn from each other until both surfaces are completely separated. Also the force during the separation phase is determined as a function of the travelling distance from the state of conformal contact until the point of becoming totally separated.

The force applied during the loading phase is summed up from the point of contact until the maximum load. This integral represents the energy stored in the elastic deformation of the pillar. The applied force during the unloading phase is similarly summed up from maximal load to zero load after backlesh compensation.

Surfaces having substances with great work of adhesion have to be pulled away from each other until these snap apart. The difference between the two energies (loading integral, unloading integral) is the work of adhesion and corresponds individually to the substance coated on the sample surface. The obtained value of the work of adhesion can now be compared with a reference value derived from stored data or a reference measurement.

Another alternative method for identification of a substance by obtaining results of high quality and expressiveness about the nature and the type of substance can be reached in the following manner:

As is the case in the aforementioned method the unknown substance is derivatized onto a sample surface which comes into contact with a contact surface onto which a well-known probe is coated. At least one of said surfaces, preferably the contact surface is made of flexible material like elastomeric material so that both surfaces come into conformal contact. Subsequently, both surfaces are withdrawn from each other by applying a defined increasing force to at least one of the surfaces until complete separation between the surfaces is reached. It is important that the involved force which is preferably directed onto the contact surface acts in a predefined manner so that the step of withdrawing can be repeated reversibly and in a standardized manner.

A value which is characteristic for the interaction between the unknown substance and the probe is the time period between commencement of applying the increasing force for withdrawing both surfaces from each other and the point of complete separation. The obtained time period is expressive of the binding forces acting between the substance and the probe and is therefore characteristic of the substance. For identification of the measured substance, the obtained time period has to be compared with a reference value which can be deduced from a stored data set or obtained by typical reference measurements.

Instead of applying a defined increasing force as is described above, in a further alternative method, a defined constant force is applied to at least one of said surfaces for the withdrawing step. Without measuring physical parameters like applied forces or time duration, it is only of interest whether both surfaces having contact or not after applying the constant force onto it.

So it is possible to classify a substance only by its binding behavior. With said constant single force action a threshold value can be determined which helps to make a rough decision whether the to-be-analyzed substance can withstand the applied force or not by checking whether both surfaces stay in contact or not.

Certainly the latter alternative just permits only a rough knowledge about the nature and the type of substance but the method can be seen as a first approach for a rough identification or distinction of substances and can be carried out in a simple way so that this method is suited for field practice.

The invention also relates to a device for identification of a substance, preferably comprising biochemical molecules, with which the inventive method can be carried out. For this, the device comprises basically two carrier means, one for the to-be-analyzed substance and the other one for the known probe. The probe is applied onto a contact surface which is a surface of a support means which preferably is molded of elastomeric material in the shape of a pillar. For a better statistic balancing of determination of the involved binding forces between the substance and the probe, the contact surface of the pillar provides a fraction of $\mu m^2$ up to several $mm^2$. On the other hand, the unknown substance is derivatized onto a sample surface which can be of rigid material such as a glass substrate.

For bringing into contact as well as for separation of both surfaces, a separation means is provided which preferably is connected with the pillar arrangement so that the pillar can be moved towards and can be withdrawn from the sample surface. In a preferred embodiment the separation means comprises a stepper motor drive which enables a controlled travelling distance between the contact surface of the pillar and the sample surface.

Further measuring means are provided for measuring, for example, applied forces which are directed onto the surfaces for bringing the surfaces into contact or for withdrawing them from each other. Likewise, the measuring means can be designed for determination of the time period between conformal contact of both surfaces and the state of complete separation. A light source might be provided for coupling light into said pillar arrangement for detecting whether the pillar stays in contact to the sample surface or being separated. For this purpose, the pillar has to be made of translucent material so that light can be coupled into the pillar, which works as a waveguide. In the event of having contact between the pillar and the sample surface, the light coupled into the pillar transmits the boundary layer between the contact surface and the sample surface into the body on which the sample surface is provided. Preferably the body of the sample surface is also made of a translucent material so that transmitted light can pass the body without suffering high losses. A detection means is arranged adjacent to the body for measuring the amount of transmitted light.

In the event of having no contact between the contact surface and the sample surface the amount of transmitted light is clearly reduced due to the reflection at the contact surface of the pillar which is surrounded by a medium having a different refraction index compared to that of the pillar material itself. With the detected signal of the light detecting means, for example realized by a CCD camera or more simply by eye, precise information can be obtained about the actual state of both surfaces whether staying in contact or being separated. This signal can be used as a start or stop signal for measuring the aforementioned time it takes to separate both surfaces. Also the light detection means can provide information about reaching the state of conformal contact between the contact surface and the sample surface.

In a further preferred embodiment the inventive device can be used as a biosensor for detection and characterization of a multiplicity of substances in the form of biomolecules. The biosensor comprises at least one pillar made of elastomeric material like polydimethylsiloxane (PDMS) having a diameter from about $0{,}1\ \mu m$ to 1 mm and an aspect ratio of about 2–10. The contact surface of the pillar is derivatized with chemical compounds comprises molecules having selective binding properties. These sensing molecules are attached to the contact surface in an oriented way so that the active side of each molecule points away from the pillar surface and can be used for selective sensing. Each molecule is strongly fixed at the contact surface and can be used many times. When the pillar is pressed onto the sample surface and forms a conformal contact, the flexibility of the pillar allows for individual molecules to recognize and bind their ligands in a specific manner typical of biological systems. When the pillar is pulled away from the sample surface, a higher force is necessary than for reference systems without specific recognition. The binding energy can be measured as pointed out above.

In a similar manner, a multiplicity of substances attached on many separate sample surfaces can be tested and classified in an automatic set up when the sample surfaces are fixed onto the bottom of a microtiter plate.

Furthermore, the biosensor can also provide a multiple pillar arrangement, each pillar having a contact surface being coated with one type of biomolecules having different selective binding properties. The pillars of the arrangement are connected by a common connection means so that contact between said contact surfaces of each pillar to a sample surface can occur simultaneously.

The approach described above for measuring biological molecules with that kind of inventive biosensor also works for mixed and dilute systems. In a dilute system the surface of the sensor is only partially covered by the substance to be analyzed. Partial coverage of the sensor surface by the substance to be analyzed can result from a too short exposure of the surface to a solution having this substance, or a small sticking coefficient between the surface and this substance. In a mixed system the substance to be identified is present on the surface of the sensor with other molecules that codeposited from a solution having several types of molecules. To this case the fraction of the sensor surface coated by the substance to identify reflects the relative sticking coefficient and concentration of the various molecules with the surface. In both cases the work of adhesion can be substantially reduced as the density of the substance to be identified on the surface decreases.

A strategy to prevent these effects is the active capture of the substance to identify from the solution to the surface using immobilized capturing molecules. In this strategy the surface of the sensor is first derivatized with a molecule that specifically binds to and immobilizes the substance to identify, concentrating it at the surface of the sensor. The advantage of this strategy commonly used in immun chemistry, for example, is the use of the possible high affinity constant and the high selectivity between the capturing molecule and the substance to identify. In this case the measured work of adhesion remains high even for dilute or mixed solutions.

DESCRIPTION OF THE DRAWINGS

The invention is described in detail below with reference to the following schematic drawings. It is to be noted that the figures are not drawn to scale.

DESCRIPTION OF PREFERRED
EMBODIMENTS

The basic concept of the present invention is described in connection with FIGS. 1–5.

Figure 1:
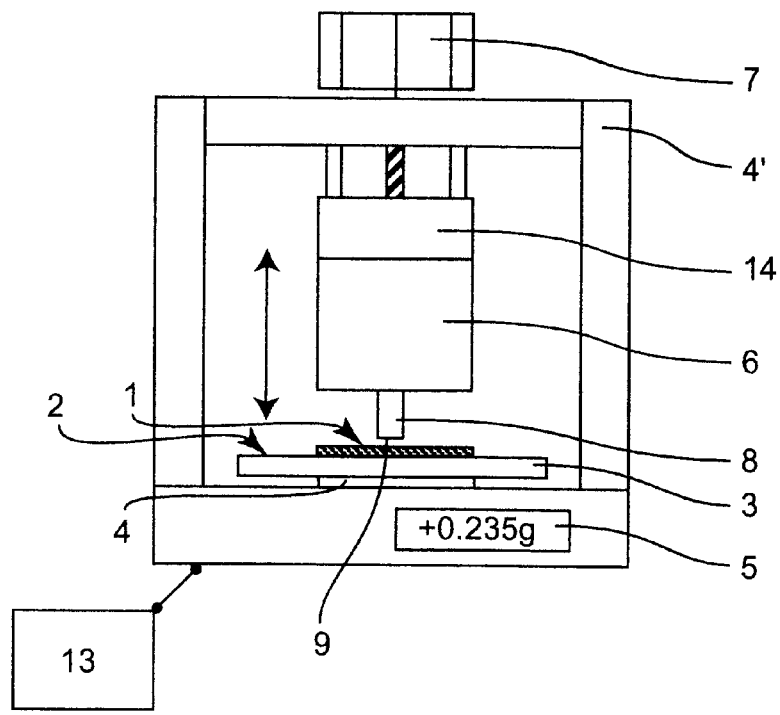
FIG. 1 illustrates a schematic side view of a device for Identification of a substance.

FIG. 1 shows a device for identification of a substance, preferably comprising biomolecules. The to be analyzed substance 1 is coated onto a sample surface 2 which can be the surface of a substrate 3 made of glass. For measuring forces which are directed vertically onto said sample surface 2, the substrate 3 is arranged preferably onto a scale 4 comprising display 5 that shows the amount of the actual force excerted on sample surface 2 as well as on the scale 4.

Mounted on a frame 4' which stays in direct contact with a basement onto which the scale 4 is arranged, a supporting means 6 is provided in a vertically moveable manner connected to a separation means 7 realized, for example, as a stepper motor drive or simply as a hand-turned screw, or a piezo element.

As will be explained later, the body of the supporting means 6 can provide a light source 14 or other means for detecting physical parameters like force sensors or tracking sensors. The supporting means 6 itself or separated from it a further body 8 is provided which is molded as a elastomeric pillar having the contact surface 9 onto which a probe p is derivatized.

By activating separation means 7, the pillar 8 is pushed towards the sample surface 2 until both surfaces come into well-defined conformal contact. As it is described above, pillar 8 together with probe p is subsequently withdrawn from the sample surface 2 in a similar manner. The force during the loading and the unloading phase, which is measured by the scale 4, is measured as a function of the travelling distance of the stepper motor drive 7. A comparing means (13) is connected to the measuring means 4 for comparing said measured physical parameter with reference values for identification.

Figure 2:
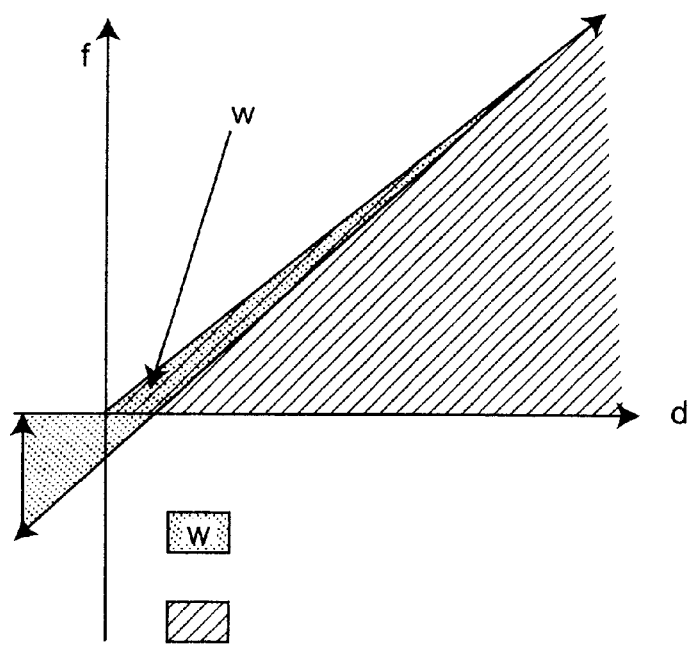
FIG. 2 illustrates a diagram of evaluating work of adhesion, FIGS. 3a,b,c illustrates a device used as a biosensor for identification of biomolecules.

As it can be seen from FIG. 2, which shows a diagram along its abscissa, the travelling distance d of the stepper motor drive is plotted and along its ordinate, the applied force is plotted, the work of adhesion can be obtained by forming the difference between the integrals over the force as a function of travelling distance applied in the loading and in the unloading phase. In FIG. 2, the hatched surface represents the integral of the loading phase, the dotted surface w in the diagram represents the work of adhesion between the substance and the probe.

Ideally, elastic pillars such as made of polydimethylsiloxanes leave these measures unaltered by the amplitude of the loading and the speed of the loading and unloading cycles. Nonideal plastic materials used for the pillar require identical speeds for the loading and the unloading cycles. The area of the contact surface of pillar 8 can be as small as a fraction of a square microns up to several square millimeters. A large contact surface of the pillar, which is in conformal contact with the sample surface, averages over many molecules and thereby provides the statistical information needed for many biosensing applications. Compared to the well-known technique of atomic force microscope (AFM), the surface of the pillar is much bigger than the tip of an atomic force microscope so that the results obtained using the aforementioned invented device depend on a statistic.

Figure 3A:
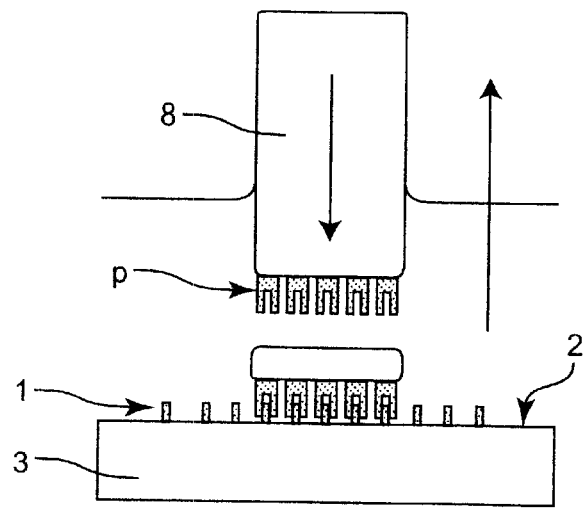

A very important aspect of the inventive device is the ability to cover the contact surface with well-known biological molecules having sensitive binding properties. So it is possible that the contact surface of the pillar is derivatized for example with a ligand that specifically captures and orients active, intact molecules and eliminates denatured or otherwise inactive molecules. This can be seen from FIG. 3a which shows an inventive device used as a biosensor. The pillar 8 is coated with a specific layer of biomolecules representing the probe p which interacts very selectively with corresponding substances 1 provided on the sample surface 2 as it is indicated in FIG. 3. The pillar 8 is subsequently pushed down onto the sample surface 2 so that the specific biomolecules of probe p interact in a chemical way with the substance 1 derivatized on the sample surface 2.

Detection works also for mixed and diluted systems although the work of adhesion can be substantially reduced as the density of the substance to be identified on the surface decreases.

Figure 3B:
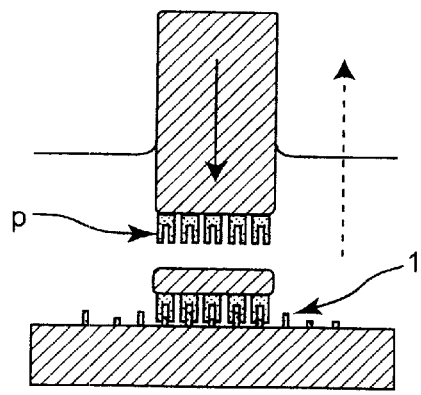

In the dilute and/or mixed system shown in FIG. 3b the surface 9 of the sensor is only partially covered by the substance 1 to be analyzed while being in contact with the sample surface 2. Partial coverage of the sensor surface 9 by the substance 1 to be analyzed can result from a too short exposure of the sample surface 2 to a solution having this substance 1, or a small sticking coefficient between the surface 2 and this substance 1.

In a mixed system the substance 1 to be identified is present on the surface 9 of the sensor with other molecules 15 that codeposited from a solution having several types of molecules. To this case the fraction of the contact surface 9 of the sensor coated by the substance 1 to identify reflects the relative sticking coefficient and concentration of the various molecules with the surface. In both cases the work of adhesion can be substantially reduced as the density of the substance to be identified on the surface decreases.

Figure 3C:
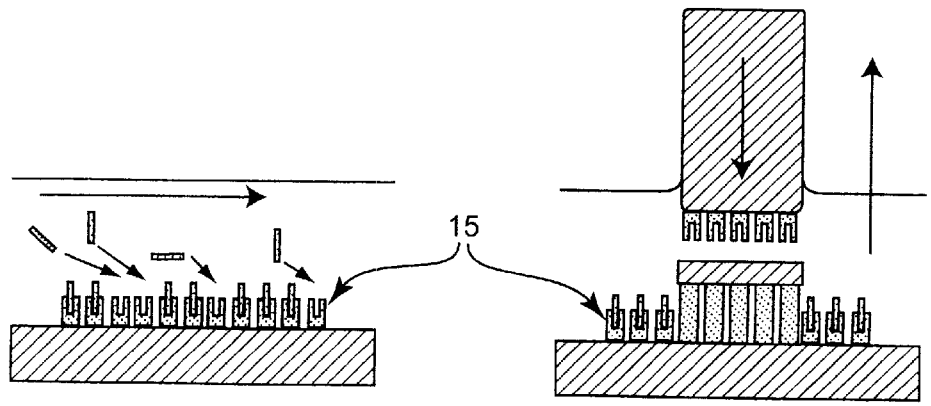

A strategy to prevent these effects is the active capture of the substance 1 to identify from the solution to the surface using immobilized capturing molecules like it is shown in FIG. 3c left an right drawing. In this strategy the surface 9 of the sensor is first derivatized with a molecule like probe p that specifically binds to and immobilizes the substance 1 to identify, concentrating it at the surface of the sensor. The advantage of this strategy commonly used in immun chemistry, for example, is the use of the possible high affinity constant and the high selectivity between the capturing molecule and the substance to identify. In this case the measured work of adhesion remains high even for dilute or mixed solutions.

Figure 4:
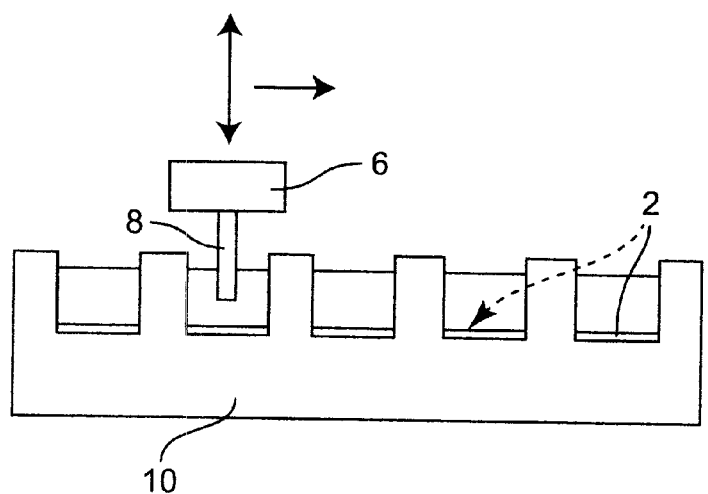
FIG. 4 illustrates an arrangement for identification of the specific biological interaction on a titer plate.

In a similar manner many of those sample surfaces 2 as is shown in FIG. 4 can be arranged on a microtiter plate 10 so that an automatic set up can test the substances 1, which are provided in each sample surface arranged on a microtiter plate 10. Consequently an automatically moved pillar 8 as indicated by the arrows can interact subsequently with various sample surfaces 2.

The embodiments of the inventive device shown in FIGS. 1, 3 and 4 are all based on balance as a force transducer. The described setups are simpler than other sensor typical approaches such as grating couplers or quartz balances. Even simpler multichannel detection can be implemented using a supporting means providing a multiplicity of single pillars preferably with diameters from a fraction of one micron to several millimeters and an aspect erasures of about ten, i.e. the pillars are ten times longer than their diameter.

Figure 5:
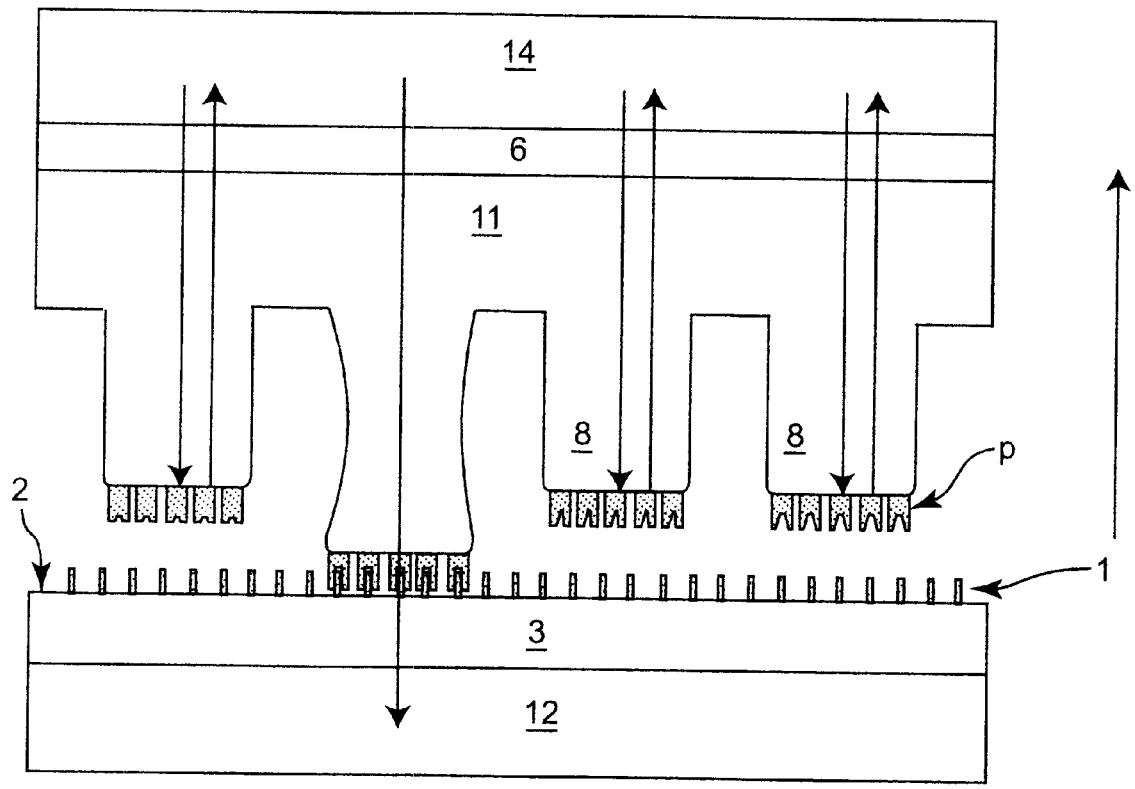
FIG. 5 illustrates a schematic side view of a biosensor using light as transduction mechanism.

Such an arrangement is shown in FIG. 5 having a supporting means 6 providing a multiplicity of single pillars 8 each connected with the others via a connection piece 11. Ideally single pillar 8 and the connection piece 11 are made of translucent PDMS.

Pillars 8 have, within a fabrication tolerance of about 1%, all the same length and are derivatized with difference sensing molecules. These pillars 8 are put into conformal contact with the sample surface 2 and after a few seconds the bulk of elastomeric pillars 8 is moved slowly away from the sample surface 8. Pillars 8 with no specific interaction immediately separate from the sample surface whereas pillars 8 with specific interaction remain in contact with the surface and stretch until the elastic force exceeds the interaction force.

For identification of the unknown substances, the work of adhesion can be determined as in the example described above by determining the accurate time of separation. Because the translucent pillars act as waveguides for light which emitted from a light source 14 separation can be easily detected using a detection means 12 like a human eye or a CCD camera positioned under the sample surface which also is made of a translucent material.

LIST OF REFERENCE NUMBERS
1 substance
2 sample surface
3 substrate
4 scale
4' frame
5 display
6 supporting means
7 separation means
8 body, pillar
9 contact surface
10 microtiter plate
11 connection piece
12 detection means
13 comparing means
14 light source
15 capturing molecules
p probe

What is claimed is:

1. A method for identifying of an unknown substance (1) in a sample comprising the steps of:
   derivatizing a sample which may contain said unknown substance (1) onto a sample surface (2),
   immobilizing a known probe (p) for said unknown substance (1) onto a contact surface (9),
   bringing said sample surface (2) and said contact surface (9) into conformal contact,
   separating said sample surface (2) from said contact surface (9) to end said conformal contact,
   measuring a value of at least one physical parameter characteristic of the binding of said known probe (p) to said unknown substance (1), and
   comparing said measured value with reference values, wherein said reference values comprise measured values of said at least one physical parameter characteristic of the binding of said known probe (p) and known substances, and wherein said step of comparing results in the identification of said unknown substance (1) by comparison to said measured values.

2. The method of claim 1, wherein said contact surface (9) is of elastic property.

3. Method according to claim 1,
   wherein said physical parameter(s) is measured, by
      applied forces directed on said unknown substance (1) and said known probe (p) during bringing into contact and withdrawing, and/or
      amount of displacement of said unknown substance (1) and said known probe (p) for bringing into contact and withdrawing and/or
      time duration between the beginning of withdrawing and complete separation of said unknown substance (1) and said known probe (p).

4. Method according to claim 1, wherein identification of said unknown substance (1) being carried out by measuring the work of adhesion between said unknown substance (1) and said known probe (p), comprising the steps of bringing said contact surface (9) into conformal contact with said sample surface (2) by applying a first force onto at least one surface in a first step, withdrawing both surfaces (2,9) from each other by applying a second force until complete separation between both surfaces is reached in a second step, measuring an amount of displacement of said moved surface being carried out such that in said first step a first amount of displacement from the situation of first contact between said both surfaces (2,9) until a state of conformal contact is measured and that in said second step a second amount of displacement from the state of conformal contact until complete separation of said both surfaces (2,9) is measured and forming integrals of said first and second force each as a function of said first and second displacement, subtracting the results of both integrals for obtaining work of adhesion.

5. Method according to claim 1, wherein identification of said unknown substance (1) being carried out by measuring a time duration between the beginning of withdrawing and complete separation of said unknown substance (1) and said known probe (p), comprising the steps of bringing said contact surface (9) into conformal contact with said sample surface (2), withdrawing both surfaces (2,9) from each other by applying a defined, increasing force on at least one of said surfaces until complete separation between both surfaces is reached, measuring said time duration and comparing said time duration with a reference value of time duration for identification.

6. Method according to claim 1, wherein identification of said unknown substance (1) being carried out by applying a defined constant force between said unknown substance (1) and said known probe (p) for withdrawing, comprising the steps of:

bringing said contact surface (9) into conformal contact with said sample surface (2), withdrawing both surfaces (2,9) from each other by applying a defined constant force on at least one of said surfaces, detecting the sate of each surface of being in contact or being separated in relation to said applied force and comparing this result with reference values for identification.

7. Device for identification of an unknown substance, comprising:

a supporting means having at least one contact surface with a diameter from 0.1 μm to 1 mm, wherein said contact surface is derivatized with a known probe specific for said unknown substance, a sample surface arranged opposite of said contact surface, wherein said sample surface is derivatized with a sample which may contain said unknown substance, a separation means connected to said supporting means and said sample surface for moving said contact surface and said sample surface into conformal contact and for withdrawing said supporting means and said sample surface from conformal contact, a detection means for detecting the situation of said surfaces being in conformal contact or separated, a measuring means to measure physical parameter(s) when bringing said surfaces into conformal contact and withdrawing said surfaces, and a comparing means for comparing said measured physical parameter(s) with reference values for identification.

8. Device according to claim 7, wherein said supporting means (6) is a molded elastomeric pillar (8).

9. Device according to claim 8, wherein said pillar (8) is of translucent material.

10. Device according to claim 8, wherein said pillar (8) is of siloxanes, especially polydimethylsiloxanes (PDMS).

11. Device according to claim 7 wherein said known probe (p) consists of known biomolecules with selective binding properties.

12. Device according to claim 9, wherein a light source (14) couples light into said pillar (8) so that said pillar (8) works as a waveguide such that a part of the light transmits the contact surface (9) of said pillar (8) and another part of the light is reflected at the contact surface (9) and said detection means (12) is arranged so as to measure the transmitted light.

13. Device according to claim 12, wherein a plurality of pillars (8) are arranged in a pattern and said light detection means (12) is a CCD-camera for detecting the transmitted light at each single contact surface (9) separately.

14. Device according to claim 8, wherein each pillar provides an aspect ratio of about 2–10, wherein each pillar is twice up to ten times longer than its diameter.

15. Device according to claim 7, wherein said separation means (7) is a stepper motor drive.

16. Device according to claim 7, wherein said separation means (7) is connected to said contact surface (9) and/or said sample surface (2) and provides a force between said both surfaces (2, 9) by moving at least one said surface to or away from said other surface.

17. Device according to claim 7, wherein said known probe (p) is specific for a biomolecule.

* * * * *